United States Patent [19]

Witter

[11] Patent Number: 4,895,717

[45] Date of Patent: Jan. 23, 1990

[54] REVERTANT SEROTYPE 1 MAREK'S DISEASE VACCINE

[75] Inventor: Richard L. Witter, Okemos, Mich.

[73] Assignee: The United States of America as represented by the Secretary of Agriculture, Washington, D.C.

[21] Appl. No.: 71,948

[22] Filed: Jul. 10, 1987

[51] Int. Cl.$^4$ .................... A61K 39/12; A61K 37/00; C12N 15/00; C12N 7/08; C12R 1/91
[52] U.S. Cl. ........................................ 424/89; 424/93; 435/172.1; 435/237; 435/948; 935/63; 935/65; 935/70
[58] Field of Search ............... 424/88, 89, 93; 435/68, 435/91, 172.1, 172.3, 235, 236, 237, 240.1, 320; 935/1, 6, 9, 11, 12, 22, 23, 24, 59, 60, 63, 65

[56] References Cited
PUBLICATIONS

R. L. Witter, "Protection by Attenuated and Polyvalent Vaccines Against Highly Virulent Strains of Merek's Disease Virus," Avian Pathol. 11: 49–62 (1982) [#S452].
R. L. Witter et al., "Polyvalent Marek's Disease Vaccines: Safety, Efficacy and Protective Synergism in Chickens with Maternal Antibodies," Avian Pathol. 13: 75–92 (1984) [#S501].
Paoletti et al., (1984) *PNAS* 81:193.

*Primary Examiner*—Jayme A. Huleatt
*Assistant Examiner*—Richard C. Peet
*Attorney, Agent, or Firm*—M. H. Silverstein; C. P. Ribando; John D. Fado

[57] ABSTRACT

A Marek's disease vaccine comprising either a revertant virus derived by backpassaging an attenuated serotype 1 Md11 virus or an antigenic component of the virus is characterized by increased levels of replicative ability and protectivity in chickens as compared to the original attenuated strain. Revertants of the invention are exemplified by a clone identified as Md11/75C/R2 and can be formulated into monovalent and polyvalent vaccines.

4 Claims, No Drawings

REVERTANT SEROTYPE 1 MAREK'S DISEASE VACCINE

BACKGROUND OF THE INVENTION

1. Field of the Invention

Vaccines have been used for the prevention of Marek's disease (MD) in commercial chickens since 1970. There are over 4 billion chickens raised annually in the United States alone. Although vaccination programs have been considered highly effective overall, the poultry industry continues to experience losses due to MD. Given the tendency of MD virus to become more virulent with time coupled with the economic pressures confronting the poultry industry, there is still a strong incentive to develop even more efficacious products that will protect better in the face of early challenge with very virulent field strains. This invention relates to a novel vaccine against MD which does in fact provide superior protection over the existing commercial vaccines.

2. Description of the Prior Art

There are three distinct serotypes of MD virus found in chickens: (1) serotype 1, the oncogenic form responsible for the disease, including high- and low-virulence MD virus and their attenuated variants; (2) serotype 2, a nononcogenic MD virus; and (3) serotype 3, herpesvirus of turkeys (HVT).

The prototype MD vaccine consists of the serotype 3 virus originally isolated from turkeys as reported in Witter et al. I. [Am. J. Vet. Res. 31: 525–538 (1970)] and Okazaki et al., U.S. Pat. No. 3,642,574. Its lack of oncogenicity, self-limiting infection, good replication in vivo and in vitro, availability as cell-free and cell-associated preparations, and high protective efficacy have established HVT as a standard for MD vaccines throughout the world. A commonly used strain of HVT is FC126.

Vaccines produced from the naturally avirulent SB-1 strain [Schat et al., J. Natl. Cancer Inst. 60: 1075–1082 (1978) and U.S. Pat. No. 4,160,024], an isolate of a serotype 2 MD virus, have been licensed in the United States since 1984. The SB-1 strain is poorly protective against the highly virulent Md5 strain. It is usually used in combination with HVT as a bivalent vaccine since the two viruses together produce greater protection than does either one alone [Schat et al. Avian Pathol. 11: 593–606 (1982); Witter, Avian Pathol 11: 49–62 (1982), herein incorporated by reference]. This phenomenon has been termed "protective synergism." The SB-1+HVT bivalent vaccine represents about 18% of the United States market for MD vaccines at present and is considered to be the most efficacious of the various MD products available. However, sporadic losses occur despite its use.

Another MD vaccine produced from strain CVI988 clone C (CVI988/C) has recently been licensed for commercial use in the United States. This vaccine is a mildly virulent serotype 1 MD virus attenuated by serial passage in tissue culture and has been reported by Rispens et al. [Avian Dis. 16: 108–125 (1972)] and deBoer et al. [Avian Dis. 30: 276–283 (1986)].

An experimental vaccine derived from Md11, a very virulent serotype 1 MD field isolate, was reported by Witter, supra. Md11 was attenuated by 75 serial passages in cell culture, and the resultant vaccine designated Md11/75C. This vaccine has been shown to provide good protection against challenge with Md5 and most other highly virulent MD viruses tested; but it was less efficacious against challenge with the JM/102W strain, a prototype MD virus effectively protected against by HVT and SB-1 vaccines. Furthermore, its efficacy was consistently lower in chicks with HVT antibody.

Thus, although HVT, SB-1, CVI988/C, and Md11/75C are all effective against certain MD viruses, none of these vaccines protect optimally against all MD challenge viruses in all chickens. In an effort to avert any large-scale outbreaks of MD in the future, the search for improved vaccines has continued.

SUMMARY OF THE INVENTION

I have now discovered a novel MD vaccine derived from an attenuated form of Md11. The attenuated strain is backpassaged in vivo to produce a revertant virus which is characterized by significantly improved replicative ability and protectivity against MD as compared to the original attenuated strain of Md11. The vaccine comprises either the revertant virus per se, or certain derivatives thereof.

In accordance with this discovery, it is an object of the invention to provide a novel, highly protective, serotype 1 vaccine against MD in chickens.

It is also an object of the invention to provide both monovalent and polyvalent vaccines against MD which are more efficacious than those presently in commercial use.

It is another object of the invention to improve the viability and productivity of chickens, particularly broilers and layers, and to reduce economic losses in the poultry industry caused by MD.

Another object of the invention is to provide an MD vaccine which is characterized by a rapid rate of replication, and thereby enhanced protective efficacy and in vitro production efficiency.

Other objects and advantages of the invention will become readily apparent from the ensuing description.

DETAILED DESCRIPTION OF THE INVENTION

"Vaccine" is defined herein in its broad sense to refer to any type of biological agent in an administratable form capable of stimulating an immune response in an animal inoculated with the vaccine. For purposes of this invention, the vaccine may comprise either the virus itself or an immunogenic (antigenic) component of the virus. The vaccine may also be produced from a vector having inserted therein a gene which encodes an immunogenic component of the virus.

The term "revertant" is intended to refer to a subculture of an attenuated virus, the subculture being characterized by increased virulence and increased in vivo replication as compared to the attenuated form. The term is used herein generically to encompass both true revertants and apparent revertants, the latter being derived from a population of viral particles rather than from a cloned virus.

The starting material for use in preparing the vaccines of the invention is any attenuated Md11 virus such as the Md11/75C virus reported by Witter, supra. The attenuation achieved by high-level serial passage in cell culture virtually eliminates the pathogenicity of the virus toward chickens. However, as reported in Witter, the efficacy of the attenuated vaccine against challenge by certain strains is minimal, especially in chickens with material antibodies. The methodology for attenuation by serial passage is well known and documented in the art.

To produce the novel vaccine, the attenuated virus is serially backpassaged through live avian hosts (i.e., chickens) as described for example by Witter et al. II [Avian Pathol. 13: 75–92 (1984), herein incorporated by reference]. As the first step of backpassaging, the host is inoculated with an infective amount of the attenuated cell culture virus stock. After becoming suitably infected by the virus, the blood or other infected tissue is used in the next stage of the backpassaging to inoculate another bird. Typically, at least about three passages of this nature are required in order to establish in the virus a level of protectivity which is significantly improved over that of the attenuated form. As noted in Witter et al. II, supra, by the third backpassage the in vivo replicative ability is increased. It is now apparent from my discovery that there is a positive correlation between increase in replicative ability and increase in protectivity against challenge viruses. Thus, replicative rate may be used as an indicator of protectivity against challenge viruses. Backpassaging may also result in increased pathogenicity. In the selection process, it is therefore necessary to evaluate each candidate strain against established criteria for acceptable levels of pathogenicity. In the event of undue pathogenicity, it is envisioned that the revertant virus can be further attenuated by serial passage or genetic manipulation. However, for chickens protected either by maternal antibodies or by generic resistance, any pathogenicity of the revertants will be limited or negligible. Moreover, based upon data collected for the Md11/75C/R2 strain described in the Examples below, the revertant viruses of the invention appear not to be spread by contact.

Candidate strains isolated from the backpassaging are preferably cloned to insure homogeneity. To prepare cell-free virus inocula for the cloning, cells from infected host tissue or cell culture are sonicated or otherwise disrupted. The cellular debris is removed by filtration and the filtrate recovered as the inoculum. Cloning is conducted on a suitable medium such as chicken embryo fibroblasts (CEF).

A cell-associated vaccine can be prepared directly from the cloning medium. For a cell-free inoculum, the virus can be isolated as previously described. It is also an embodiment of the invention to prepare vaccines from the killed virus or from immunogenic components separated from the virus.

As previously mentioned, the gene or genes encoding the immunogenic component or components responsible for the protective ability of the revertant virus can be inserted into a suitable vector system by recombinant techniques as known in the art. The methodology involving recombinant DNA techniques has now become routine in science and has been successfully demonstrated in analogous applications [E. Paoletti et al., Proc. Natl. Acad. Sci. U.S.A. 81: 193–197 (1984)]. Specifically, the process would first involve the identification of proteins or other components of the revertant that are critical to the induction of protective immunity. Next, specific regions of the viral genome (genes) along with any endogenous promoters would be identified and characterized through mapping with restriction endonucleases and determination of the nucleotide sequences. The identified gene or genes would then be spliced into expression vectors such as bacterial plasmids (to produce a killed protein product) or live viruses such as avian herpesviruses or avian poxviruses (to produce a live recombinant DNA vaccine virus). Other types of expression vectors could also be used. Once properly constructed with the necessary promoter sequences, the expression vector will produce the product of the inserted gene, namely the critical immunizing protein or proteins of the revertant. If produced by a vector grown in vitro, the immunizing protein will be obtained from the culture medium, purified, and used with appropriate adjuvants and diluents as a killed vaccine for the immunization of chickens. Other vectors, chosen for their natural infectivity for chickens, will be inoculated directly into chickens as a recombinant live virus vaccine. The vaccine will then produce the immunizing protein in vivo, thus causing protection directly and without the need for additional inoculations.

The viral agent is prepared for administration by formulation in an effective immunization dosage with a pharmaceutically acceptable carrier or diluent, such as physiological saline or tissue culture medium. The expression "effective immunization dosage" is defined as being that amount which will induce immunity in a chicken against challenge by a virulent strain of MD. Immunity is considered as having been induced in a population of chickens when the level of protection for the population is significantly higher than that of an unvaccinated control group. One measure of the level of protection is the protective index (PI), which is calculated as the MD in unvaccinated, MD virus challenged controls minus the MD in vaccinated, MD virus challenged groups, and the difference divided by the percent MD in unvaccinated, MD virus challenged controls, with the result multiplied by 100. Typically, the vaccine will contain at least about 1000 PFU (plaque-forming units) of the virus, and preferably between 2000 and 5000 PFU. The vaccine can be effectively administered anytime after the chicken attains immunocompetence, which is at about the 18th day of incubation (3 days prehatch); but it is normally administered by inoculation within 24–48 hr after hatching.

Appropriate adjuvants as known in the art may also be included in the vaccine formulation. In many cases, the vaccinal efficacy can be enhanced by combining the Md11 revertant with other viral agents into bivalent or polyvalent vaccines.

The following examples are intended only to further illustrate the invention and are not intended to limit the scope of the invention which is defined by the claims.

EXAMPLE 1

Three revertant clones useful as vaccines in accordance with this invention were prepared as follows: An attenuated Md11 virus designated Md11/75C (representing any of passage levels 75–79) was obtained by serial passage of the virulent Md11 on CEF as described by Witter, supra.

Following the procedure of Witter et al. II, supra, chickens selected for backpassaging were $F_1$ progeny of Regional Poultry Research Laboratory line $15I_5$ males and line $7_1$ females. The line $15I_5$ males and $7_1$ females obtained at breeding age were not vaccinated and were held in isolation as part of the laboratory breeding flock. By periodic serologic tests, the flock was found to be free of antibodies to MD virus, HVT, avian leukosis virus, reticuloendotheliosis virus, and other common poultry pathogens. The progeny chickens were not vaccinated.

Chickens in the initial passage received 2000 PFU of the 79th passage cell culture virus stock. At 4 weeks, four donors were selected, bled, and necropsied. The blood was pooled and used to inoculate a second group of 1-day-old chicks. Buffy coat cells from the pooled inoculum were assayed for virus. The remaining chickens were held for 10 weeks and were necropsied. This procedure was repeated for 10 passages. Histological examination of peripheral nerves and the gonad was performed on all donor chickens and on the 10-week-old survivors in certain passages. The results are reported in Table I below.

TABLE I

Pathogenicity of Md11/75C During Backpassage in Susceptible Chickens

| Backpassage No. | Viremia[a] (4 weeks) | MD lesions (4 weeks) Gross | MD lesions (4 weeks) Micro | MD lesions (10 weeks) Gross | MD lesions (10 weeks) Micro |
|---|---|---|---|---|---|
| 1 | 4.0 | 0/4 | 0/4 | 0/11 | ND[b] |
| 2 | 10.5 | 0/4 | 0/4 | 0/11 | ND |
| 3 | 50.5 | 0/4 | 0/4 | 1/11 | ND |
| 4 | 64.0 | 0/4 | 0/4 | 2/11 | ND |
| 5 | 63.0 | 0/4 | 1/4 | 1/7 | 3/7 |
| 6 | 74.0 | 0/4 | 0/4 | 0/4 | 1/4 |
| 7 | 86.5 | 0/4 | 1/4 | 1/11 | 7/11 |
| 8 | 63/5 | 0/4 | 0/4 | 1/11 | 3/11 |
| 9 | 69.5 | 0/4 | 0/4 | 2/11 | 4/11 |
| 10 | ND | ND | ND | 2/13 | 7/13 |

[a]Mean PFU/$10^6$ buffy coat cells, one pooled sample tested each passage.
[b]ND = not done.

A "revertant" virus was isolated from the fourth chicken passage (Md11/75C/R) and was subsequently cloned using cell-free virus inocula obtained from sonicated and filtered cell cultures. This clone was taken to the 87th serial passage on CEF (counting from the last cell culture passage prior to backpassaging) for purposes of multiplication, and it was designated as Md11/75C/R2. This strain was deposited in the American Type Culture Collection in Rockville, MD, and assigned Accession No. ATCC VR2175. Revertant viruses cloned directly from backpassages 6 and 9 were taken to serial passage 86, and designated Md11/75C/R5 and Md11/75C/R8, respectively.

EXAMPLE 2

The various clones isolated in Example 1 were compared to parent and control strains for pathogenicity and protective efficacy. The pathogenicity tests were conducted on maternal antibody negative (ab-) chickens. These were $F_1$ progeny of line $15I_5$ males and line $7_1$ females that received no vaccinations and were held in positive pressure, flexible canopy isolators as part of the laboratory specific pathogen-free flock. These breeders were free of antibodies to MD virus, HVT, avian leukosis virus, reticuloendotheliosis virus, and other common poultry pathogens.

A single pathogenicity test was conducted in ab- chickens which were inoculated by the intraabdominal route at 1 day posthatch with 2000 PFU of appropriate test viruses. Groups of 16 chickens were held by inoculum in separate Horsfall-Bauer type isolators. Eight chickens were removed and bled at 3 weeks of age; the remaining eight chickens were killed at 8 weeks, bled, weighed, and necropsied. The gonad, vagus, and brachial nerves were examined for histological lesions. The blood samples were slow centrifuged, and the buffy coat cells in the supernatant were assayed for virus.

For the virus assay, standard methods for the isolation of viruses of serotypes 1, 2, and 3 were used. Pathogenic serotype 1 isolates were grown and assayed in DEF whereas other viruses were grown and assayed in CEF cultures. Virus plaques were enumerated within 2 days of first appearance, usually between 3 and 8 days post inoculation; this time varied between viral strains but was a constant for a particular virus strain.

Protection tests utilized groups of 20 ab+$F_1$ progeny from breeders ($15I_5$ males $\times 7_1$ females) vaccinated with vaccine viruses of all three serotypes, i.e., Md11/75C (serotype 1), SB-1 (serotype 2), and FC126 (serotype 3), at a dose of 1000 PFU for each virus. Sera were obtained from these breeder flocks at several intervals during lay and tested for MD antibodies. The flocks were held in isolation pens and were not intentionally exposed to virulent serotype 1 viruses.

The test chickens which were inoculated by the intraabdominal route at 1 day posthatch with 2000 PFU of appropriate vaccines. Control groups were vaccinated with FC126 and JM/102W. A nonvaccinated group was also evaluated. Each group was held in a separate Horsfall-Bauer type isolator. Challenge with virulent Md5 virus was done 5 days post vaccination with inoculum administered intraabdominally at a dose of 500 PFU per chick. The groups were held for about 56 days post challenge, killed, necropsied, and the presence of gross MD lesions recorded. Birds dying during the experiment were examined for gross lesions. The birds considered to be at risk were those positive for MD lesions plus those survivors without lesions. A protective index was calculated as the percent MD in unvaccinated, challenged controls minus the percent MD in vaccinated, challenged groups divided by the percent MD in unvaccinated, challenged controls multiplied by 100. The results are reported in Table II below. The presence of precipitating antibodies in chickens at 10 weeks post incubation indicated that the Md11/75C/R2 clone has retained the "A" antigen.

As shown in Table II, all four revertant viruses induced MD lesions with up to 50% frequency (histological) and at least two viruses depressed body weights, but all were much less pathogenic than JM/102W. Protection against Md5 challenge was similar for the three clones, and each clone provided higher protection than the parent revertant.

TABLE II

Comparative Evaluation of Revertant Md11/75C Clones

| Virus strain | Viremia, PFU/$10^6$ WBC 3 Weeks | Viremia, PFU/$10^6$ WBC 8 Weeks | Pathogenicity (8 weeks) No. chicks | Mort | MD lesions Gross | MD lesions Histo | Body weights | Protection vs. Md5 +MD/Total | Protective index |
|---|---|---|---|---|---|---|---|---|---|
| Md11/75C | 2.5 | ND | 8 | 0 | 0 | 0 | 700.5 | 14/20 | 30 |
| Md11/75C/R | 46.6 | 11.3 | 7 | 0 | 1 | 1 | 650.1 | 10/19[C] | 47 |
| Md11/75C/R2 | 43.3 | 11.3 | 8 | 0 | 1 | 3 | 614.3[A] | 5/19[BC] | 74 |
| Md11/75C/R5 | 31.7 | 13.1 | 8 | 0 | 3 | 4 | 651.8 | 6/20[BC] | 70 |
| Md11/75C/R8 | 61.0 | 12.6 | 8 | 0 | 0 | 4 | 619.9[A] | 7/20[BC] | 65 |
| FC126 | 27.4 | ND | 8 | 0 | 0 | 0 | 657.8 | 18/20 | 10 |
| JM/102W | 74.9 | ND | 8 | 3 | 8 | 8 | 273.5[A] | ND | — |

TABLE II-continued

| | Comparative Evaluation of Revertant Md11/75C Clones | | | | | | | | |
|---|---|---|---|---|---|---|---|---|---|
| | Viremia, PFU/10⁶ WBC | | Pathogenicity (8 weeks) MD lesions | | | | | Protection vs. Md5 | |
| Virus strain | 3 Weeks | 8 Weeks | No. chicks | Mort | Gross | Histo | Body weights | +MD/Total | Protective index |
| None | ND | ND | 16 | 0 | 0 | 0 | 662.5 | 20/20 | — |

A Differs ($P < 0.05$) from uninoculated control group by Bonferroni t-test.
B PI greater ($P < 0.05$) compared to Md11/75C by Chi-square analysis.
C PI greater ($P < 0.05$) compared to FC126 by Chi-square analysis.

EXAMPLE 3

This experiment was designed to compare the long-term pathogenicity of Md11/75C/R2 in chickens with and without maternal antibodies. The ab- chickens were the same as those used in Example 2. The ab+ chickens were $F_1$ progeny of RPRL line $15I_5$ males and line $7_1$ females in which the females had been vaccinated with all three MD viral serotypes (Md11/75C, SB-1, and HVT).

Groups of chickens were inoculated with virus by the intraabdominal route. In Trial 1, all inoculations were at 1 day of age. In Trial 2, the ab+ chickens were inoculated with Md11/75C/R2 and a trivalent (Md11/75C/R2+301B/1+FC126) vaccine at 1 day of age, and the Md5 positive controls were inoculated at 6 days of age. Vaccine 301B/1 is the subject of commonly assigned copending application Ser. No. 70/71,949, filed on July 10, 1987. Each group was held in separate high security negative pressure (Trial 1) or plastic canopy positive pressure (Trial 2) isolators for about 17 weeks. At termination all birds were weighed and necropsied. The body weights were adjusted for sex differences by multiplying female weights by a factor computed by dividing the mean of all male weights by the mean of all female weights. DNA from blood of certain tumor-bearing chickens was analyzed by restriction enzyme analysis with the conclusion that they were not induced by inadvertent exposure to a virulent wild-type serotype 1 virus. The results are reported in Table III below.

The degree of the observed pathogenicity was much less than that of Md5, a very virulent pathotype of MD virus. Thus, Md11/75C/R2 should be considered as mildly pathogenic in ab- chickens, comparable in pathogenicity to the uncloned revertant Md11/75C.

EXAMPLE 4

To test for the rate of contact transmission of the Md11/75C/R2 revertant clone of Example 1 as compared to other viruses, uninoculated chickens (ab-) were intermingled with the groups of 30 other chickens of Example 3 which had been inoculated with 20,000 PFU of virus. At 10 weeks of age, the uninoculated birds were removed and bled. Viruses were isolated from the sera by standard methods. Antibodies were detected in sera by the agar gel precipitin test using an antigen prepared from the feather tips of chickens infected with a virulent serotype 1 MD viral isolate. The results are reported in Table IV below.

EXAMPLE 5

Chickens from each of the groups in Example 3 vaccinated with Md11/75C/R2, CVI988/C, and FC126 were bled at termination (17 weeks) and tested for viremia persistence. Buffy coat cells were assayed for virus by standard procedures on CEF or DEF cultures. The results are reported in Table V below. Compared to CVI988/C, strain Md11/75C/R2 induced viremias of much higher titer and at a greater frequency.

EXAMPLE 6

The protectivity of various serotype 1 and serotype 2 vaccines against challenge with serotype 1 viruses was determined essentially as described in Example 2. JM/102W/48 is an attenuated strain of JM/102W as described by Witter et al. III [J. Natl. Cancer Inst. 62: 143–151 (1979)]. The protective efficacy of each virus was evaluated against challenge with JM/102W and Md5 in two different trials, each using 20 birds per group. In a third trial, each virus was used with FC126 as a bivalent vaccine and challenged with a mixture of virulent viruses using 40 birds per group; protection was compared to that provided by the FC126 vaccine

TABLE III

| | | Long-Term Pathogenicity Test of Vaccine Viruses | | | | | |
|---|---|---|---|---|---|---|---|
| Trial | Chicken type | Vaccine | PFU dose | No. birds | MD lesions % Mort | MD lesions % Gross[a] | Body weights[b] |
| 1 | 15 × 7 ab− | Md11/75C/R2 | 20,000 | 32 | 9.3 | 28.1 | 1453.4 |
| | | Md11/75C/R2 | 2,000 | 31 | 3.2 | 19.4 | 1435.6 |
| | | Md11/75C/R2 + FC126 | 2,000[c] | 34 | 2.9 | 11.8 | 1429.7 |
| | | CVI988/C | 20,000 | 33 | 0.0 | 0.0 | 1491.4 |
| | | FC126 | 20,000 | 34 | 0.0 | 0.0 | 1500.5 |
| | | Md5 | 1,000 | 34 | 100.0 | 100.0 | — |
| | | None | 0 | 32 | 0.0 | 0.0 | 1485.1 |
| 2 | 15 × 7 ab+ | Md11/75C/R2 | 20,000 | 35 | 0.0 | 0.0 | 1609.4 |
| | | Md11/75C/R2 + FC126 + 301B/1 | 20,000[c] | 27 | 0.0 | 0.0 | 1571.0 |
| | | Md5 | 500[d] | 31 | 100.0 | 100.0 | — |
| | | None | 0 | 23 | 0.0 | 0.0 | 1604.8[a] |

[a]Includes mortality.
[b]Means within the same trial do not differ ($P < 0.05$) by Bonferroni t-tests.
[c]Aggregate PFU dose, divided equally among constituent viruses.
[d]Inoculated at 6 days of age; all other groups inoculated at day 1.

included as an internal control in each experiment. The results are reported in Table VI below. It is apparent that the Md11/75C/R2 virus provided excellent protection alone against JM/102W and Md5 challenge and, at least in one trial, significantly augmented the protective efficacy of FC126.

TABLE IV

Evaluation of Vaccine Viruses for Transmission by Direct Contact

| Virus | Transmission frequency | |
|---|---|---|
| | Virus isolation | Antibody |
| Md11/75C/R2 | 0/9 | 0/10[a] |
| CVI988/C | 0/8 | 4/10 |
| FC126 | 0/10 | 4/10 |
| Md5 | 3/3 (9.0)[b] | 4/4 |
| None | 0/10 | 0/10 |

[a]Sera from Md11/75C/R2-inoculated birds were positive for agar gel precipitin antibodies.
[b]Mean PFU isolated per $2 \times 10^6$ buffy coat cells in parenthesis.

TABLE V

Viremia Persistence 17 Weeks After Inoculation with Vaccine Viruses

| Virus | PFU dose | Virus isolation | |
|---|---|---|---|
| | | +/Total | Mean PFU[a] |
| Md11/75C/R2 | 20,000 | 11/11 | 111.0[A] |
| CVI988/C | 20,000 | 2/12 | 0.1[B] |
| FC126 | 20,000 | 2/12 | 0.2[B] |

[a]Per $2 \times 10^6$ buffy coat cells. Means with different superscripts differ ($P < 0.05$) by Bonferroni t-tests.

TABLE VI

Protective Efficacy

| Serotype | Virus strain | Passage | Protection vs. JM/102W | | Protection vs. Md5 | | Augmentation of HVT protection[a] | | |
|---|---|---|---|---|---|---|---|---|---|
| | | | PI | Compare vs. HVT PI | PI | Compare vs. HVT PI | PI | % of HVT PI | Compare vs. HVT |
| 1 | JM/102W/48 | 48 | 31 | —[b] | 52 | ns[b] | 49 | 114 | ns[b] |
| | Md11/75C | 79 | 34 | — | 17 | ns | 54 | 126 | ns |
| | Md11/75C/R | 82 | 63 | ns | 68 | ns | 63 | 107 | ns |
| | Md11/75C/R2 | 87 | [94][c] | ns | [52] | nd | [75] | 288 | + |
| 2 (low) | SB-1/1 | 23 | 93 | ns | 57 | ns | 53 | 136 | ns |
| 2 (med) | SB-1/1 | 64 | 69 | ns | 0 | — | 30 | 136 | ns |
| 2 (high) | SB-1/1 | 98 | 38 | — | 1 | — | 26 | 118 | ns |

Abbreviations: PI = protective index; HVT = FC126 strain of turkey herpesvirus.
[a]Challenged with a mixture of JM/102W, Md5, and 287L; 1000 PFU aggregate dose.
[b]Results of Chi-square analysis: ns = not significant ($P > 0.05$); + = PI greater than HVT control ($P < 0.05$); − = PI less than HVT control ($P < 0.05$); nd = not analyzed because data from internal HVT control was not available.
[c][ ] = PI values of viruses selected for further analysis as the best representatives of their class.

slightly different designs: chickens in Trials 9 and 10 were challenged with Md5 but a 1 day by contact, or at 11 days by inoculation. Trial 11 utilized a commercial White Leghorn chicken strain with Md5 challenge at 5 days post vaccination. Trial 12 differed from the others because only five vaccines were tested, groups contained 40 chickens, and the experimental period was 17 weeks post challenge.

There was close agreement in the results of the various series. Although each experiment was not a direct replicate, the similarity in design and the comparability of results permitted consolidation of the results into Table VII below. The protective efficacy (61.5%) of Md11/75C/R2 as a monovalent vaccine in Trials 1-11 was significantly greater than FC126, SB-1, 301B/1, and CVI988/C ($P < 0.05$), and approximated that of the FC126+SB-1 bivalent. In the 17-week trial (Trial 12), Md11/75C/R2 provided significantly ($P < 0.05$) better protection than the FC126+SB-1 bivalent vaccine. The trivalent composed of FC126+301B/1+Md11/75C/R2 consistently provided the best protection of any vaccine (mean protection 85.6%, range 65-100%) and ranked first in five of eight trials.

Data from Trials 1-11 were used to compare paired protection data from the two serotype 1 viruses, CVI988/C and Md11/75C/R2. A paired comparison represents data from two lots in the same trial where treatment variables were identical except for the use of the indicated viruses as the vaccines (Table VIII). By these analyses Md11/75C/R2 was clearly superior to CVI988/C.

EXAMPLE 7

To further evaluate the vaccines contemplated by the invention, Md11/75C/R2 was compared in a series of protection trials to commercial and other experimental vaccines. These trials were conducted essentially as described in Example 2, except as noted below. The dose for polyvalent vaccines was the same in aggregate (2000 PFU) as for monovalent vaccines, with each constituent virus equally represented. In the first series (Trials 1-4), 14 vaccines were evaluated including six monovalent, seven bivalent, and one trivalent products. Control groups either received a placebo consisting of normal CEF at a concentration equivalent to that of other vaccines or were nonvaccinated. Chickens in each trial were challenged with a different virulent or very virulent serotype 1 MD virus; Md5, RB1B, 287L, and 295. In the second series (Trials 5-8), the number of vaccines was reduced to nine but otherwise was identical to the first series. In the third series (Trials 9-12), the same nine vaccines were evaluated but the trials had

EXAMPLE 8

Viruses were tested for growth rate at 3 days post inoculation and plaque size at 5 days post inoculation in CEF cultures as previously described by Witter et al. IV [Avian Dis. 24: 210-232 (1980)]. Fifteen plaques were measured for each virus. To determine cell-free virus production, CEF cultures were inoculated with high doses of cell-associated virus and harvested by trypsinization 2 to 3 days post inoculation when cytopathic effects were maximum. One portion of the culture was assayed for cell-associated virus in the usual way. The other portion was suspended in SPGA buffer, sonicated for 60 sec in three 20-sec thrusts at a power setting of 100 w with a "Braun-sonic" 1510 sonifier, and centrifuged at $15,600 \times g$ for 3 min. The top one-half of the supernatant was carefully removed, titrated in SPGA buffer, and assayed by inoculation of drained CEF monolayer cultures. After absorption for 20 min at 38° C., growth medium was added and the cultures maintained under standard conditions until plaque could be enumerated. The data are expressed as the number of cell-free PFU recovered per $10^6$ cell-associated PFU. The results are reported in Table IX below. As measured by 3-day growth rates, Md11/75C/R2 grew five times faster than CVI988/C and 18 times faster than SB-1. Plaque size and cell-free virus production was also greater for Md11/75C/R2 than for either CVI988/C or SB-1.

It is understood that the foregoing detailed description is given merely by way of illustration and that modification and variations may be made therein without departing from the spirit and scope of the invention.

TABLE IX

Growth Characteristics of Vaccine Viruses in CEF Cultures

| Virus | Growth rate[a] | Plaque size[b] | Cell-free virus production[c] |
|---|---|---|---|
| Md11/75C/R2 | 270.0 | 0.234[A] | 475 |
| CVI988/C | 53.7 | 0.125[B] | 8 |
| SB-1 | 14.7 | 0.022[C] | 77 |

[a]Number of PFU per input PFU 3 days after inoculation.
[b]Mean area in $mm^2$ of 15 virus plaques measured 5 days after inoculation. Means with different superscripts are different (P <0.05) by Bonferroni t-tests.
[c]Number of cell free PFU recovered 2-3 days after inoculation per $10^6$ cell-associated PFU.

I claim:

1. A vaccine comprising: (1) in an effective immunization dosage a viral agent wherein said viral agent is a cloned revertant virus having the essential identifying characteristics of Md11/75C/R2 produced by back-passaging attenuated strain Md11/75C and is characterized by significantly improved protectivity against Marek's disease as compared to said attenuated strain, and (2) a pharmaceutically acceptable carrier or diluent.

2. A vaccine as described in claim 1 wherein said viral agent is a live revertant virus in a cell-associated preparation.

3. A method for protecting a chicken against Marek's diseases comprising inoculating said chicken with an effective immunization dosage of a viral agent in a pharmaceutically acceptable carrier or diluent, wherein said viral agent is a cloned revertant virus having the essential identifying characteristics of Md11/75C/R2 produced by backpassaging attenuated strain Md11/75C and is characterized by significantly improved protectivity against Marek's disease as compared to said attenuated strain.

4. A method as described in claim 3 wherein said viral agent is a live revertant virus in a cell-associated preparation.

TABLE VII

Statistical Analysis of Vaccine Efficacy

| Vaccine | MD+/Total | Mean PI ± ± SEM | Greater than[a] HVT | BiV | CVI | SB-1 | None |
|---|---|---|---|---|---|---|---|
| FC126 | 140/213 | 30.4 ± 4.7 | — | — | — | — | ABC |
| SB-1 | 135/217 | 33.7 ± 4.1 | — | — | — | — | ABC |
| 301B/1 | 120/214 | 40.2 ± 5.9 | — | — | B | — | ABC |
| CVI988/C | 147/212 | 26.2 ± 4.7 | — | — | — | — | ABC |
| Md11/75C/R2 | 79/212 | 60.1 ± 7.1 | ABC | — | ABC | ABC | ABC |
| FC126 + SB-1 | 85/216 | 58.6 ± 5.2 | ABC | — | ABC | ABC | ABC |
| FC126 + 301B/1 | 55/207 | 71.6 ± 4.4 | ABC | AB | ABC | ABC | ABC |
| FC126 + SB-1 + Md11/75C/R2 | 56/213 | 72.6 ± 4.5 | ABC | AB | ABC | ABC | ABC |
| FC126 + 301B/1 + Md11/75C/R2 | 19/138 | 85.6 ± 3.8[b] | ABC | AB | ABC | ABC | ABC |
| None | 196/209 | — | | | | | |

Abbreviations: MD+ = birds positive for Marek's disease lesions; PI = protective index; SEM = standard error of the mean; HVT = FC126 strain of turkey herpesvirus; BiV = bivalent (FC126 + SB-1) vaccine; CVI = CVI988/C.
[a]Statistical analysis by three methods: A = Vaccine PI greater (P < 0.05) than indicated vaccine by Youden index analyses; B = Vaccine PI greater (P < 0.05) than indicated vaccine by Chi-square analyses; C = Vaccine PI greater (P < 0.05) than indicated vaccine by Bonferroni t-tests.
[b]Analyzed separately on basis of data from Trials 5-11.

TABLE VIII

Analysis of Paired Comparisons in Eleven Trials

| Vaccine | Total pairs | Mean PI[a] | Comparisons[b] Greater | Equal |
|---|---|---|---|---|
| Md11/75C/R2 | 19 | 56.4[A] | 14[A] | 2 |
| CVI988/C | 19 | 30.3[B] | 3[B] | 2 |

[a]Mean protective index values with different superscripts within the same pair group are different (P <0.05) by Bonferroni t-tests.
[b]Number of paired comparisons in which the PI of the designated virus was greater, lesser, or equal to the alternate virus. Values with different superscripts are different (P <0.05) by Chi-square analysis.